(12) United States Patent
Fukunaga

(10) Patent No.: US 6,231,935 B1
(45) Date of Patent: May 15, 2001

(54) FUNCTIONAL MAN-MADE ORNAMENTAL PLANTS AND A METHOD FOR MANUFACTURE THEREOF

(75) Inventor: Toshikazu Fukunaga, Hyogo (JP)

(73) Assignee: Yugen Kaishi Fukuji Corporation, Hyogo (JP)

( * ) Notice: Subject to any disclaimer, the term of this patent is extended or adjusted under 35 U.S.C. 154(b) by 0 days.

(21) Appl. No.: 09/060,215

(22) Filed: Apr. 15, 1998

(30) Foreign Application Priority Data

Apr. 15, 1997 (JP) .................................................. 9-096860

(51) Int. Cl.⁷ ........................................................ A41G 1/00
(52) U.S. Cl. ................................ 428/17; 428/24; 428/905
(58) Field of Search ................................ 428/17, 24, 905

(56) References Cited

U.S. PATENT DOCUMENTS

| | | | |
|---|---|---|---|
| 369,878 | * 8/1887 | Palmer | 239/55 |
| 387,466 | * 9/1888 | Watson | 206/457 |
| 1,538,631 | * 5/1925 | Francis | 206/457 |
| 1,644,482 | * 10/1927 | Muller | 239/47 |
| 1,647,533 | * 11/1927 | Matlack | 239/327 |
| 1,886,429 | * 11/1932 | Saeks | 239/60 |
| 1,989,883 | * 2/1935 | Redwine | 239/44 |
| 3,861,991 | * 1/1975 | Kim | 428/13 |
| 4,293,602 | * 10/1981 | Coffey et al. | 428/28 |
| 4,708,851 | * 11/1987 | Freytag Von Loringhoven | 422/123 |
| 4,950,542 | * 8/1990 | Barker | 428/403 |
| 4,957,787 | * 9/1990 | Reinhardt et al. | 428/24 |
| 5,077,102 | * 12/1991 | Chong | 428/24 |
| 5,183,656 | * 2/1993 | Uesaka et al. | 424/76.1 |
| 5,282,572 | * 2/1994 | Fuller | 239/56 |
| 5,459,920 | * 10/1995 | Huang | 29/458 |
| 5,547,823 | 8/1996 | Murasawa et al. | 430/531 |
| 5,690,922 | * 11/1997 | Mouri et al. | 424/76.1 |
| 5,776,561 | * 7/1998 | Lindauer | 428/24 |

\* cited by examiner

Primary Examiner—Lyle A. Alexander
Assistant Examiner—LaToya I. Cross
(74) Attorney, Agent, or Firm—Armstrong, Westerman, Hattori, McLeland & Naughton, LLP

(57) ABSTRACT

A first functional man-made ornamental plant comprises a foliage-floral part L of a man-made ornamental plant having a thin layer AB of a composition comprising an inorganic particulate substance having photocatalyst activity (a) and a binder which is inorganic or has been made inorganic (b) preferably on top of an under-coat layer B of the binder which is inorganic or has been made inorganic (b). A second functional man-made ornamental plant is characterized in that the foliage-floral part L of a man-made ornamental plant is molded from a composition comprising a matrix resin and, as incorporated therein, an inorganic particulate substance having photocatalyst activity (a). Preferably, the surface of the molded foliage-floral part L is delicately roughened.

2 Claims, 2 Drawing Sheets inorganic particulate substance

FUNCTIONAL MAN-MADE ORNAMENTAL PLANTS AND A METHOD FOR MANUFACTURE THEREOF

TECHNICAL FIELD

The present invention relates to a functional man-made ornamental plant with excellent deodorizing and other environment-decontaminating performance characteristics.

PRIOR ART

The concept of environmental decontamination such as deodorization, disinfection and cleaning of indoor atmosphere has by now pervaded through all the ecosystems inclusive of homes, offices, factories, schools, hospitals, other public buildings, traffic facilities, and so on.

As a handy deodorizer which does not require any special ancillary equipment, an ornamental deodorizer is in broad use for the purpose of deodorizing small spaces within the closet, showcase, refrigerator, locker, passenger car, toilet room, and other compartments. Typical deodorizers of this type consist of a gas-permeable housing and, as packed therein, an adsorbent material such as activated charcoal or a gel containing an aromatic chemical or deodorant. Since deodorizers of this type can be expected to play the role of interior ornaments as well, they are available in various fashionable designs.

Meanwhile, as a mechanically sophisticated deodorizer, there is known an air cleaner comprising a motor, a fan, and a deodorizing filter as built into the pot of an artificial foliage plant.

Inorganic powders having photocatalyst activity, such as titanium dioxide particles, are attracting attention these days and have been applied in the field of disinfection and deodorization. For example, it is reported that by spray-coating tiles or sanitation fixtures with an inorganic powder and baking the coat, a semi-permanent disinfectant effect can be achieved [Nikkei Business, Mar. 21, 1994 issue, pp. 60–61; Trigger, May 1994 issue, pp. 84–85].

Handy deodorizers of the above-described type are convenient because the desired deodorizing effect can be achieved by installing it as a mere interior ornamental ment but is self-limited in effectiveness, with the deodorizing activity being lost or drastically decreased generally within about 1–2 months.

On the other hand, the above more sophisticated deodorizer comprising a motor, a fan, and a deodorizing filter as built into the pot of an artificial foliage plant is a modification of the conventional air cleaner for home use but the equipment is not only costly but has the drawback that the motor noise is a nuisance during night hours and in quiet surroundings.

The inorganic powders having photocatalyst activity have just begun to find application in the form of a baked-on enamel for tiles and sanitation fixtures but the deodorizing effect of the coat is not remarkable although the effect of inhibiting growth of deposited bacteria may be more or less satisfactory. Thus, since the surface area of the inorganic particles having photocatalyst activity has been reduced by baking, the duration of contact with odor components is presumably too brief to decompose them.

Recently several proposals have been made to support photocatalyst inorganic powders on a honeycomb and use the honeycomb as an air cleaner filter to achieve deodorization and, at the same time, build a UV lamp into the air cleaner to activate the catalyst. However, those are not beyond mere contrivances and cannot be considered to be practically useful equipment from the standpoint of hardware cost, necessity of a power supply, and motor noise.

OBJECT AND SUMMARY OF THE INVENTION

The present invention has for its object to provide a functional man-made ornamental plant which, despite not including an air cleaner device, achieves an excellent deodorizing effect, is capable of decomposing organic foulants, with the deodorizing and antifouling effects being long-lasting, and is soothing both visually and mentally because of its naturalness and a process for manufacture thereof.

A first functional man-made ornamental plant according to the invention comprises a foliage-floral part L of a man-made ornamental plant having a thin layer AB of a composition comprising an inorganic particulate substance having photocatalyst activity (a) and a binder which is inorganic or convertible to an inorganic substance (b). Preferably, the thin layer AB is formed from said inorganic particulate substance having photocatalyst activity (a) and binder which is inorganic or convertible to an inorganic substance (b) on top of an under-layer B of a binder which is inorganic or has been made inorganic (b).

A second functional man-made ornamental plant according to the present invention is characterized in that the foliage-floral part L of a man-made ornamental plant is molded from a composition comprising a matrix resin and, as incorporated therein, an inorganic particulate substance having photocatalyst activity (a). Preferably, the surface of the molded foliage-floral part L has been delicately roughened.

A process for manufacturing the functional man-made ornamental plant according to the present invention comprises contacting the foliage-floral part of a man-made ornamental plant or a precursor thereof with a composition comprising an inorganic particulate substance having photocatalyst activity, a binder which is inorganic or convertible to an inorganic substance, and a vehicle capable of dispersing or dissolving them to thereby form said thin layer AB. Preferably, the process comprises contacting the foliage-floral part L of a man-made ornamental plant or a precursor thereof with a composition comprising a binder which is inorganic or convertible to an inorganic substance and a vehicle capable of dispersing or dissolving it in the first place to construct a base coat B and then forming said thin layer AB on top of the base coat B.

Another process for manufacturing a functional man-made ornamental plant according to the invention comprises fabricating a foliage-floral part L from a blank or precursor molded from a composition comprising a matrix resin and, as incorporated therein, an inorganic particulate substance having photocatalyst activity (a) and assembling a man-made ornamental plant using the foliage-floral part L. Preferably, in the blank stage immediately after said molding or fabrication of said foliage-floral part L, at least one side of the blank or foliage-floral part L is finely roughened.

DETAILED DESCRIPTION OF THE INVENTION

Figure 1:
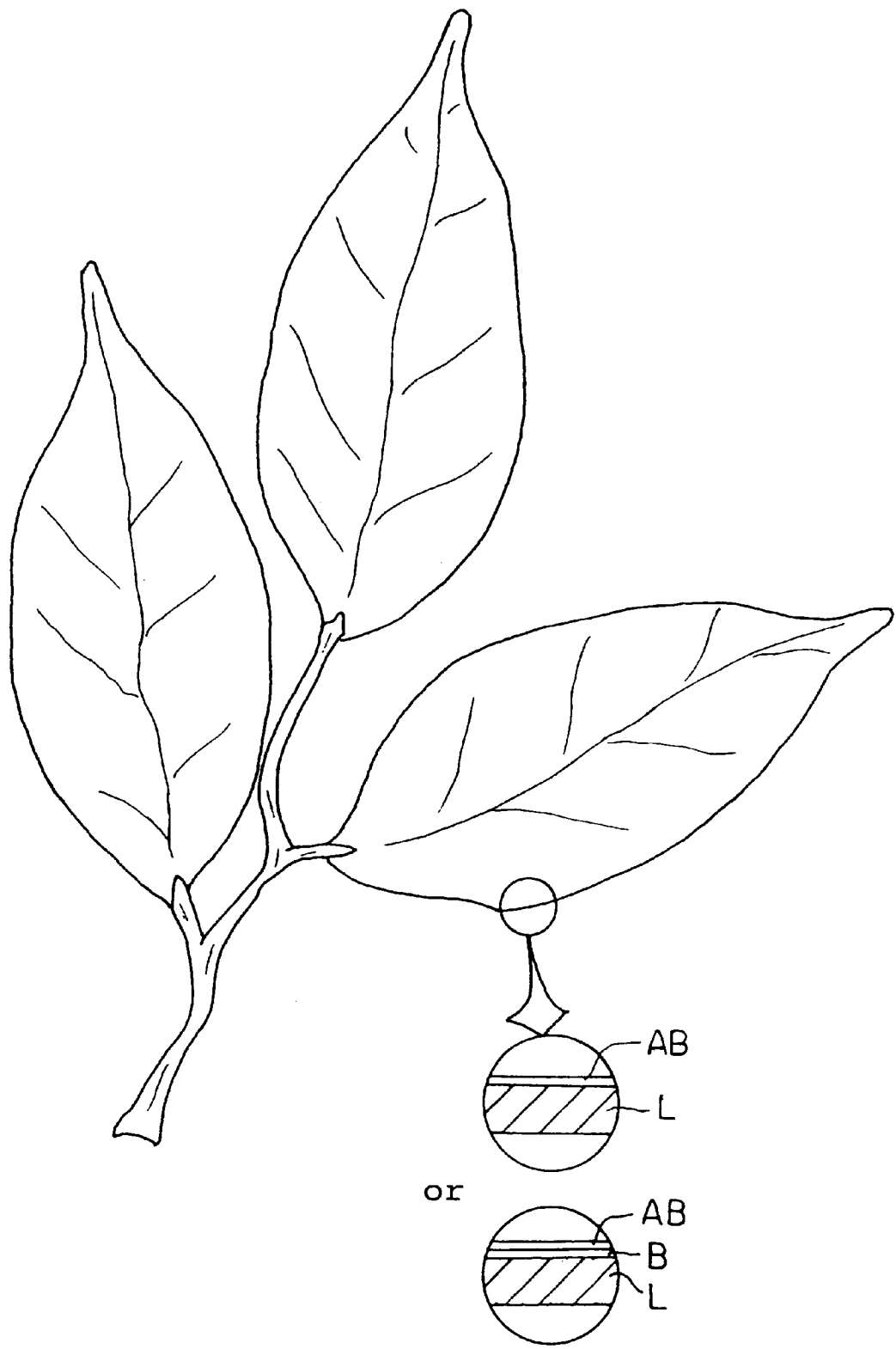
FIG. 1 is a sketch illustrating a typical twig portion of the functional man-made ornamental plant according to the invention.

The present invention is now described in detail.
Foliage-floral Part (L) of a Man-made Ornamental Plant A variety of man-made ornamental plants are available. In the case of a shrub-type product, its trunk and boughs are made of resin-processed natural trunk and branches, while its twigs and leaves are usually artifacts simulating the corresponding parts of a natural plant. Thus, the twigs are wire-cored plastic parts and the leaves are made of woven or nonwoven cloth, with veins and other details being formed by resin-coating or embossing. In the case of an artificial plant consisting entirely in foliage, the cloth material resin-treated or -embossed to form veins and other details or the resin moldings are used in many instances. The same is true of the bract and floral parts. As other man-made ornamental plants, natural grasses dried so as to retain the original shapes and colors are also used. The term "foliage-floral part" is used in this specification to mean at least one of the leaf, flower, and bract.

A First Functional Man-made Ornamental Plant and a Process for Manufacture Thereof The first functional man-made ornamental plant according to the invention is such that the foliage-floral part L of a man-made ornamental plant is provided with a thin layer AB of a composition comprising an inorganic powder (a) having photocatalyst activity and a binder which is inorganic or has been converted to an inorganic substance. In addition to the foliage-floral part L, the branches and trunk may also be provided with the thin layer AB.

The deposition of the thin layer AB on the foliage-floral part L of a man-made ornamental plant or a precursor thereof can be achieved as follows. The foliage-floral part L is contacted with a composition comprising (1) an inorganic particulate substance having photocatalyst activity, (2) a binder which is either inorganic or convertible to an inorganic substance, and (3) a vehicle for dispersing or dissolving them and, then, dried. The above contacting operation can be carried out the coating, dipping, spraying, or other method.

The thickness of the thin-layer AB on the foliage-floral part L or a precursor thereof should be limited to not over 1 $\mu$m, particularly 0.3–0.5 $\mu$m, per treatment from the standpoint of adhesion. If a single layer AB is insufficient to insure the necessary deodorizing effect, the above deposition procedure can be repeated.

The inorganic particulate substance having photo-catalyst activity includes but is not limited to ultrafine titanium dioxide powders with an X-ray particle diameter of, for example, not over 100 nm, and such powders whose surface has been modified with a metal (e.g. gold, silver, copper, platinum, zinc, silicon, iron, etc.) or a metal compound (e.g. zinc oxide, silicon oxide, etc.) can also be used with advantage.

The binder which is either inorganic or convertible to an inorganic substance includes conventional inorganic binders such as alumina sol, silica sol, etc.; alkoxysilanes such as tetramethoxysilane, tetra-ethoxysilane, trimethylmethoxysilane, methyltrimethoxy-silane, methyltriethoxysilane, etc., inclusive of their oligomers; and other metal alkoxides. After coating of the composition, alkoxysilanes are readily hydrolyzed to give silanol groups which, in turn, undergo condensation to form $SiO_2$ which is an inorganic substance. The composition may contain an organic binder, in addition to said binder which is either inorganic or convertible to an inorganic substance, only if its amount is only nominal, that is to say not large enough to contradict the object of invention. However, since the organic binder tends to be decomposed by the inorganic particulate substance having photocatalyst activity, it is usually not recommendable to use an organic binder.

The vehicle which can be used includes water, water-miscible organic solvents, and mixtures of water with water-miscible organic solvents. Particularly preferred is a mixture of water and an alcohol (e.g. methanol, ethanol, isopropyl alcohol, etc.).

The concentration of nonvolatile matter in the composition may range from about 3 to 30 weight % and is preferably about 5–20 weight % but this range need not be strictly adhered to. If the concentration of nonvolatile matter is too high, the composition can be diluted with the above-mentioned vehicle before using. The weight ratio of the inorganic particulate substance having photocatalyst activity to the inorganic binder in the composition is generally 20:80 through 95:5, preferably 30:70–90:10, in many cases. If the proportion of the binder is too small, the thin layer AB tends to be exfoliated from the surface of the foliage-floral part L or a precursor thereof. On the other hand, if the proportion of the binder is too large, the relative amount of the inorganic powder having photo-catalyst activity will be too small to insure the desired deodorizing and other performance.

When the above conditions are satisfied, the thin layer AB is substantially transparent and resists exfoliation even when rubbed against with fingers. Moreover, despite the existence of the thin layer (AB), there is obtained a functional man-made ornamental plant with the original appearance and handle of the foliage-floral part L being fully retained.

In this connection, when the thin layer AB made from a composition comprising said inorganic particular substance (a) and binder (b) is directly formed on the foliage-floral part L of a man-made ornamental plant or a precursor thereof, there is the possibility that the organic foliage-floral part L or precursor will be decomposed by the inorganic powder (a) having photo-catalyst activity in the composition. Therefore, it is preferable, in most cases, to form said thin layer AB composed of inorganic powder (a) and binder (b) only on top of a base layer B of the binder which is inorganic or has been converted to an inorganic substance. A preferred composition for the base layer B is the balance of the above-mentioned composition comprising (1), (2) and (3) after elimination of (1).

A Second Functional Man-made Ornamental Plant and a Process for Manufacture Thereof In the second functional man-made ornamental plant according to the present invention, the foliage-floral part L of a man-made ornamental plant is molded from a resin in which said inorganic particulate substance having photocatalyst activity (a) has been incorporated. In this connection, not only the foliage-floral part L but also the branches and trunk may be made from such a composition.

The foliage-floral part L is usually fabricated from a plastic sheet or a synthetic woven or nonwoven fabric. Therefore, the inorganic particulate substance having photocatalyst activity (a) is incorporated in a matrix resin in the stage of production of the sheet or synthetic fabric.

The proportion of the inorganic particulate substance having photocatalyst activity (a) in the molding may for example be 0.1–40 weight %, preferably 0.5–30 weight %, and more preferably 1–20 weight %. If the proportion of the inorganic particulate substance having photocatalyst activity (a) is too small, the deodorizing effect will be inadequate. If it is too large, the mechanical strength of moldings will be sacrificed.

When the composition comprising a matrix resin and said inorganic particulate substance (a) having photo-catalyst activity as incorporated therein is simply molded, the amount of the inorganic particulate substance (a) exposed on the surface of moldings may happen to be too small to achieve the desired deodorizing and other performance. Therefore, in the manufacture of a man-made ornamental plant using the foliage-floral part (L) fabricated from the blank molding, it is preferable to apply a surface roughening treatment to at least one side of the blank just molded or the foliage-floral part (L) elaborated from the blank.

The surface roughening treatment mentioned above includes electrical treatment, optical treatment, mechanical treatment, and chemical treatment. Among those treatments, electrical treatment, particularly plasma treatment, is preferred. The plasma treatment includes low-temperature plasma treatment, corona discharge treatment, glow discharge treatment, plasma jet treatment, etc. and, among them, low-temperature plasma treatment and corona discharge treatment are advantageous. In particular, corona discharge treatment is preferred from the standpoint of equipment cost and running cost.

The low-temperature plasma treatment includes direct current discharge treatment, alternating current-low frequency treatment, high-frequency discharge treatment, and microwave discharge treatment. As ion species constituting the plasma, various inorganic or organic gases such as air, nitrogen, oxygen, hydrogen, argon, helium, neon, nitrous oxide, nitrogen monoxide, nitrogen dioxide, carbon monoxide, carbon dioxide, fluorine, chlorine, bromine, sulfurous acid gas, hydrogen sulfide, ammonia, methane, ethane, propane, etc. can be employed. Usually, however, it is sufficient to employ air as an ion source. The degree of vacuum for said low-temperature plasma treatment may for example be about 0.01–10 Torr. The treatment time varies widely according to the degree of vacuum used but is generally several seconds to about 10 minutes. If prolonged too much, however, the low-temperature plasma treatment may adversely affect the strength of moldings.

The corona discharge treatment comprises disposing an electrode connected to a high voltage generator and a metal roll with a gap of about 0.5–0.6 mm, applying a high-voltage, high-frequency current of a few thousand to tens of thousand volts and several hundred kilo-cycles/S to generate a high-voltage corona discharge across the gap, and causing a sheet molding to travel through the gap. By this treatment, the surface of the sheet molding is activated.

As examples of optical treatment, chemical treatment and mechanical treatment, among said surface roughening treatments, there can be mentioned UV irradiation, ozone treatment, cathode sputter etching, ion beam treatment, flame treatment, chromate treatment, alkali treatment, sand blasting, and sculpturing with a cutter edge, needle, or file.

In the tree, shrub, grass, or flower, inclusive of ornamental plants, the steric configuration of the foliage thereof insures a maximal exposure of the man-made plant to light and a free passage of winds. Therefore, the plant is allowed to assimilate carbon dioxide most efficiently to thereby clean the air. Moreover, their balance (phyllotaxic structure), shape, color, feeling, and variegation are pleasing both to the eye and to the touch and soothing to one's mind.

The functional man-made ornamental plant of the present invention duplicates the leaf arrangement and image of a live plant as an adjunct means for deodorization, adding a function of deodorization to the intrinsic ornamental value of the man-made plant.

Thus, in the functional man-made ornamental plant of the invention, wherein the inorganic particulate substance having photocatalyst activity has been coated on, or incorporated in, its foliage-floral part L, the deodorizing function of the inorganic particles having photocatalyst activity is constantly restored as the light from interior fluorescent or incandescent light sources or the sunlight entering from windows impinges efficiently on the foliage-floral part L, with the result that the odorous components of the atmospheric air coming into contact with the foliage-floral part L are effectively decomposed. Moreover, the organic deposits from odoriferous tobacco smoke and kitchen smoke and fumes on the foliage-floral part L are effectively decomposed and the settling microorganisms are also destroyed. Furthermore, those effects are long-lasting. In addition, since the steric configuration of the foliage-floral part L insures a maximal exposure of the man-made plant to light and a free passage of winds, the environmental cleaning function mentioned above is maximized.

In the first functional man-made ornamental plant according to the invention, wherein the binder forming the thin layer AB is either inorganic or has been converted to an inorganic substance, the thin layer AB is not degraded even under the strong oxidative influence of the inorganic powder having photocatalyst activity. Moreover, when the thin layer AB is indirectly formed on the foliage-floral part L or a precursor thereof through a base-coat layer B of the binder (b) which is either inorganic or has been converted to an inorganic substance, the foliage-floral part L is protected against the degradation due to the inorganic particulate substance having photocatalyst activity in the thin layer AB.

Referring to the second functional man-made ornamental plant according to the invention, when at least one side of the blank just molded or the foliage-floral part L elaborated therefrom is delicately roughened as mentioned hereinbefore, the area of contact of the foliage-floral part L with the atmosphere is considerably increased so that the deodorization and cleaning function of the man-made ornamental plant can be maximized. In this second functional man-made ornamental plant, the incorporated inorganic powder having photocatalyst activity may gradually decompose the organic matter constituting the foliage-floral part L but this influence is limited to the face side only and not necessarily a detracting factor, for the pattern of this decomposition looks like the process of growth of a natural plant.

Since the functional man-made ornamental plant of the invention not only has a useful environmental decontaminating function as mentioned above but gives a sense of naturalness so that it is visually pleasing and mentally soothing. Even though the inorganic powder having photocatalyst activity has been coated on, or incorporated in, the foliage-floral part L, this man-made ornamental plant is not factually different from the conventional man-made ornamental plant in appearance, feeling, color, gloss, and other characteristics.

In addition, since the functional man-made ornamental plant of the present invention does not require a mechanical system for operation but discharges its functions when it is simply installed in a room or a car compartment, it is free from problem of motor noise and is advantageous cost-wise, too.

The following examples illustrate the present invention in further detail.

EXAMPLE 1

First Functional Man-made Ornamental Plant

Referring to FIG. 1 which illustrates a typical twig part of the functional man-made ornamental plant according to the invention, $L_1$ represents a leaf, B represents a base coat, and AB represents a thin layer.

As the composition comprising an inorganic powder having photocatalyst activity, a binder which is either inorganic or convertible to an inorganic substance, and a vehicle for dispersing or dissolving them, the photo-catalyst titanium oxide-coating system ST-K03 available from Ishihara Sangyo Co., Ltd. was used. ST-K03 has a nonvolatile matter content of 10 weight % and a $TiO_2$/binder weight ratio of 50/50. The solvent is a mixture of ethanol and water, the pH is 1.5 and the viscosity is 5 cps.

As the coating composition for construction of the base coat B, the balance of the above composition after elimination of the photocatalyst inorganic powder was used.

As a man-made ornamental plant (*Ficus benjamiana*), a twig X carrying one small leaf with a surface area of 10 cm² and two vehicle-sized leaves with a surface area of 13 cm² each and a twig Y carrying 3 large leaves with a surface area of 18 cm² each were provided. Using a brush, the above-mentioned photocatalyst titanium oxide-coating system ST-K03 was evenly coated over the surface of the foliage $L_1$ and dried to construct a thin layer AB. In addition, the twigs X and Y were dipped in the same photocatalyst titanium oxide-coating system ST-K03, withdrawn, and dried to construct a thin layer AB on each twig. In both cases, the thickness of the thin layer per coat was about 0.4–0.5 µm.

In a 5-L glass vessel equipped with a black light installed within, the above-treated twig X and twig Y, or a total of 2 twigs, were placed (total surface area of one side of the foliage ($L_1$): 90 cm²) and the vessel was closed tight. The black light, in lieu of sunlight or interior lighting, was used to insure a constant light output that is necessary for exact serial determination of odorous component concentrations.

Odorous gas (ammonia, acetaldehyde, trimethylamine or acetic acid) was injected from the top of the glass vessel and the black light was turned on. Immediately thereafter and after 2, 4, and 6 hours, the gas in the head space was sampled and the odorous component concentration was measured with a sensor tube. A control experiment was carried out using untreated twigs X and Y. The results of this deodorization experiment are shown in Tables 1–4.

TABLE 1

| | | Concentration of ammonia (ppm) | | | |
|---|---|---|---|---|---|
| | | Initial | 2 Hr | 4 Hr | 6 Hr |
| Untreated | | 50 | 50 | 49 | 48 |
| Brush-coated on one side | Once | 53 | 28 | 21 | 12 |
| | Twice | 52 | 22 | 12 | 5 |
| Dipping | Once | 55 | 23 | 16 | 10 |
| | Twice | 53 | 18 | 8 | 3 |

TABLE 2

| | | Concentration of acetaldehyde (ppm) | | | |
|---|---|---|---|---|---|
| | | Initial | 2 Hr | 4 Hr | 6 Hr |
| Untreated | | 32 | 33 | 32 | 32 |
| Brush-coated on one side | Once | 32 | 18 | 13 | 7 |
| | Twice | 30 | 14 | 7 | 2 |

TABLE 3

| | | Concentration of trimethylamine (ppm) | | | |
|---|---|---|---|---|---|
| | | Initial | 2 Hr | 4 Hr | 6 Hr |
| Untreated | | 120 | 115 | 105 | 100 |
| Brush-coated on one side | Once | 120 | 80 | 57 | 35 |
| | Twice | 120 | 64 | 30 | 12 |

TABLE 4

| | | Concentration of acetic acid (ppm) | | | |
|---|---|---|---|---|---|
| | | Initial | 2 Hr | 4 Hr | 6 Hr |
| Untreated | | 31 | 30 | 30 | 30 |
| Brush-coated on one side | Once | 30 | 22 | 18 | 12 |
| | Twice | 30 | 20 | 13 | 5 |

A base coat B was first formed on either side of the foliage $L_1$ by dipping the same twigs as above in the base coating composition and dried. Then, the above-mentioned photocatalyst titanium oxide-coating system ST-K03 was applied to the foliage $L_1$ by brush-coating or dipping to construct a thin layer AB on top of the base coat. In this case, too, the results were comparable to those shown in the above Tables 1–4. When such a base layer B is constructed, the inorganic particulate substance having photocatalyst activity is prevented from contacting directly with the foliage $L_1$ so that the man-made ornamental plant may enjoy an extended serviceable life.

The foliage plant as tall as the average human body height, for example *Ficus benjamiana* which is a representative foliage plant to be placed near the window admitting sunlight, has approximately 1000 leaves with a surface area of about 15 cm² each. This means that the total surface area on one side of the foliage $L_1$ is about 15000 cm². Therefore, one or two pots are sufficient to clean a small room.

Second Functional Man-made Ornamental Plant

EXAMPLE 2

Figure 2:
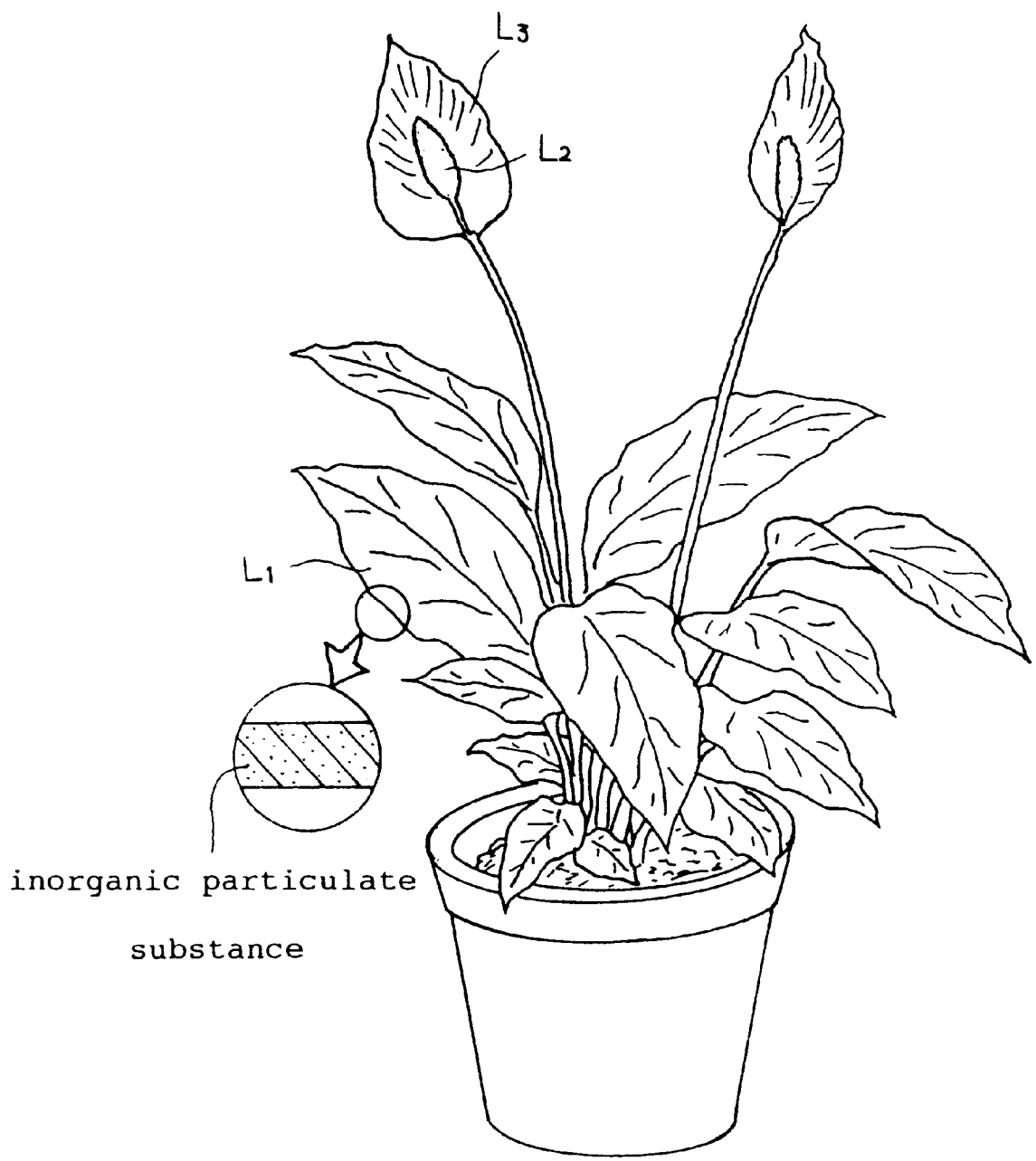
FIG. 2 is a sketch illustrating another functional man-made ornamental plant according to the invention.

Referring to FIG. 2 which illustrates another functional man-made ornamental plant of the invention, $L_1$ represents a leaf, $L_2$ represents a floral part and $L_3$ represents a bract which is a modified foliage. The inorganic powder having photocatalyst activity is indicated by dots.

As an example of the inorganic particulate substance having photocatalyst activity (a), the photo-catalyst titanium oxide ST-31 available from Ishihara Sangyo Co., Ltd. was provided. According to the company's catalog, ST-31 is an anatase crystalline powder with a $TiO_2$ content (as dried at 110° C.) of 81 weight %, an X-ray particle diameter of 7 nm, and a specific surface area (expedient BET method) of 260 m²/g.

This photocatalyst titanium oxide was incorporated in flexible polyvinyl chloride at a level of 5 weight % and the composition was molded into a sheet. Both sides of this sheet were subjected to corona discharge treatment with Kasuga Denki Company's corona discharge equipment. The treated sheet was cut to size and somewhat curled by secondary processing to fabricate a foliage $L_1$. Separately, the floral $L_2$ and bract $L_3$ parts for the conventional man-made foliage plant were provided.

In a 5-L glass vessel in which a black light was installed, the above foliage part $L_1$ (total surface area per side: 100 cm², total surface area of both sides: 200 cm²) and the floral part L₂ and bract part L₃ were placed and the vessel was closed tight.

Ammonia gas, as an example of odorous gas, was introduced from the top of the vessel and the black light was turned on. Immediately thereafter and after 2, 4, and 6 hours, the gas in the head space was sampled and the ammonia concentration was serially measured using a sensor tube. As control, the foliage part (L₁) of the same surface area as fabricated from a sheet without incorporation of the photocatalyst titanium oxide and the foliage part L₁ having the same surface area as fabricated after corona discharge treatment of a blank sheet molded without incorporation of the photocatalyst titanium oxide were also respectively put in the glass vessel together with said floral part L₂ and bract part L₃ and the same experiment was carried out. The results are shown in Table 5.

TABLE 5

|  | Concentration of ammonia (ppm) | | | |
| --- | --- | --- | --- | --- |
|  | Initial | 2 Hr | 4 Hr | 6 Hr |
| TiO₂ not incorporated | | | | |
| Without corona discharge | 55 | 51 | 47 | 48 |
| With corona discharge | 55 | 51 | 43 | 41 |
| TiO₂-incorporated | | | | |
| Without corona discharge | 52 | 41 | 32 | 24 |
| With corona discharge | 54 | 32 | 21 | 14 |

It is clear from Table 2 that the man-made plant molded from a photocatalyst titanium dioxide-incorporated resin composition has a large deodorizing effect. In contrast, when the photocatalyst titanium dioxide was not incorporated, the deodorizing effect was poor even when corona discharge treatment was carried out.

Thus, in the functional man-made ornamental plant of the invention, wherein the inorganic particulate substance having photocatalyst activity has been coated on, or incorporated in, its foliage-floral part L, the deodorizing function of the inorganic particles having photocatalyst activity is constantly restored as the light from interior fluorescent or incandescent light sources or the sunlight entering from windows impinges efficiently on the foliage-floral part L, with the result that the odorous components of the atmospheric air coming into contact with the foliage-floral part L are effectively decomposed. Moreover, the organic deposits from odoriferous tobacco smoke and kitchen smoke and fumes on the foliage-floral part L are effectively decomposed and the settling microorganisms are also destroyed. Furthermore, those effects are long-lasting. In addition, since the steric configuration of the foliage-floral part L insures a maximal exposure of the man-made plant to light and a free passage of winds, the environmental cleaning function mentioned above is maximized.

Since the functional man-made ornamental plant of the invention not only has a very useful environmental cleaning function as mentioned above but gives a sense of naturalness so that it is visually pleasing and mentally soothing. Even though the inorganic particulate substance having photocatalyst activity has been coated on, or incorporated in, the foliage-floral part L, the ornamental plant is not factually different from the conventional man-made ornamental plant in appearance, feeling or handle, color effect, gloss, and other characteristics.

In addition, since the functional man-made ornamental plant of the present invention does not require a mechanical system for operation but discharges its functions when it is simply set in a room or a car compartment, it is free from the problem of motor noise and is advantageous cost-wise, too.

What is claimed is:

1. A functional man-made ornamental plant having an organic foliage or foliage-plus-floral part comprising
    a layer constructed from a composition comprising ultrafine titanium dioxide-based photocatalyst powders with an X-ray particle diameter of not over 100 mn and an inorganic binder on an organic foliage or foliage-plus-floral part of a man-made ornamental plant,
    wherein the weight ratio of the ultrafine titanium dioxide-based photocatalyst powders to the inorganic binder is 20:80 through 95:5.

2. The functional man-made ornamental plant according to claim 1 wherein said layer has been constructed on said organic foliage or foliage-plus-floral part through a base coat layer formed beforehand from an inorganic binder.

* * * * *